United States Patent
Menon et al.

(10) Patent No.: US 9,538,991 B2
(45) Date of Patent: Jan. 10, 2017

(54) INTEGRATED MR IMAGING AND INTERVENTIONAL COIL DEVICE, METHOD AND SYSTEM

(75) Inventors: Ashok Menon, Shorewood, WI (US); Liang Liu, Pewaukee, WI (US); Dean Kenneth Walters, Hubertus, WI (US); Richard John Kurlinski, Jefferson, WI (US); Faiz Abul Ikramulla, Round Lake, IL (US); Theodore John Reisker, Hartland, WI (US); Adam Chandler Morris, Milwaukee, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 73 days.

(21) Appl. No.: 14/342,456

(22) PCT Filed: Aug. 29, 2012

(86) PCT No.: PCT/IB2012/054432
§ 371 (c)(1),
(2), (4) Date: Mar. 3, 2014

(87) PCT Pub. No.: WO2013/041994
PCT Pub. Date: Mar. 28, 2013

(65) Prior Publication Data
US 2014/0213886 A1    Jul. 31, 2014

Related U.S. Application Data

(60) Provisional application No. 61/536,175, filed on Sep. 19, 2011.

(51) Int. Cl.
*A61B 5/05*    (2006.01)
*A61B 10/00*   (2006.01)
(Continued)

(52) U.S. Cl.
CPC .......... *A61B 10/0041* (2013.01); *A61B 5/055* (2013.01); *A61B 5/708* (2013.01); *A61B 10/0275* (2013.01);
(Continued)

(58) Field of Classification Search
CPC . A61B 10/0041; A61B 10/0275; A61B 5/055; A61B 5/708; G01R 33/285
(Continued)

(56) References Cited

U.S. PATENT DOCUMENTS 5,678,549 A    10/1997    Heywang-Koebrunner et al.
5,855,554 A *  1/1999    Schneider ............ A61B 6/0414
                                                     378/37
(Continued)

FOREIGN PATENT DOCUMENTS

JP    2000107152 A    4/2000

*Primary Examiner* — Sanjay Cattungal

(57) ABSTRACT

MR imaging and intervention functions are localized within a single device. At least one integrated coil device (62,63, 64,90) which has at least one RF coil (72,94,112,118), a housing (70,74,92,96,110,114) which encases the RF coil and provides an anatomically conformal surface, and a plurality of apertures. The integrated coil device slides along a guide rail system (66) to adjust the size of a patient anatomical imaging region (60). The apertures in the integrated coil device are available to secure tool holder grid plate inserts (67,116,130,131) or other interventional device guides. The inserts assist in holding the soft tissue for diagnostic imaging and provide support for biopsy/interventional instrument guides (140). The integrated MR imaging and interventional coil device works in combination with a prone patient support structure (20), an adaptive torso sling (55), and also features an open architecture design for improved patient access. The device also works for supine or side imaging procedures.

19 Claims, 12 Drawing Sheets

(51) Int. Cl.
 *A61B 10/02* (2006.01)
 *G01R 33/28* (2006.01)
 *G01R 33/34* (2006.01)
 *A61B 5/055* (2006.01)
 *A61B 5/00* (2006.01)

(52) U.S. Cl.
 CPC ....... *G01R 33/285* (2013.01); *G01R 33/34084* (2013.01)

(58) Field of Classification Search
 USPC .................................................. 600/407–430
 See application file for complete search history.

(56) References Cited

U.S. PATENT DOCUMENTS

| | | |
|---|---|---|
| 7,379,769 B2 * | 5/2008 | Piron .................. A61B 8/0825 5/601 |
| 7,852,080 B2 | 12/2010 | Takamori et al. |
| 7,970,452 B2 | 6/2011 | Piron et al. |
| 8,366,634 B2 | 2/2013 | Leimbach et al. |
| 2001/0039378 A1 | 11/2001 | Lampman et al. |
| 2005/0080333 A1 * | 4/2005 | Piron .................. A61B 8/0825 600/417 |
| 2008/0204017 A1 | 8/2008 | Takamori et al. |
| 2009/0024020 A1 | 1/2009 | Swaminathan et al. |
| 2010/0099978 A1 | 4/2010 | Geppert et al. |

\* cited by examiner

INTEGRATED MR IMAGING AND INTERVENTIONAL COIL DEVICE, METHOD AND SYSTEM

CROSS-REFERENCE TO PRIOR APPLICATIONS

This application is the U.S. National Phase application under 35 U.S.C. §371 of International Application No. PCT/IB2012/054432, filed on Aug. 29, 2012, which claims the benefit of U.S. Provisional Patent Application No. 61/536,175 filed on Sep. 19, 2011. These applications are hereby incorporated by reference herein.

The present application relates to the magnetic resonance arts. It finds particular application in conjunction with devices and methods for the screening, diagnosis, and intervention of breast cancer.

Breast cancer is a fatal disease caused by the growth of cancerous cells within breast tissue. There cancerous cells form a lump, cyst, lesion, or the like that can grow at an alarming rate and, if left undetected, can even spread beyond the breast. Mammography and physical examination is currently the method of choice for screening and diagnosing breast cancer or other breast malignancy. In mammography, low-dose X-rays are used to generate a radiograph of the breasts. However, other breast imaging exams are often used to supplement the mammogram when further evaluation is necessary. For example, an ultrasound is typically used for further evaluation of masses found on the mammogram or palpable masses not seen on the mammogram. Though more costly than x-ray mammography, magnetic resonance imaging (MRI) is more sensitive and can detect lesions at an earlier stage than tradition x-ray mammography. Furthermore, MRI does not suffer from the high false negative rate of x-ray mammography. This is partly due to dense tissues obscuring the cancer or malignancy and the fact that the appearance of cancer on x-ray mammograms has a large overlap with the appearance of normal tissues.

In an MRI or MR spectroscopy (MRS) examination, the patient is subjected to a uniform magnetic field which aligns nuclear spins of the body tissue along an axis, typically the z-axis in a Cartesian coordinate system. The aligned nuclear spins are then excited by transverse magnetic fields $B_1$ oscillating in the radiofrequency band. In imaging, relaxation signals are exposed to gradient magnetic fields to localize the resultant resonance. The relaxation signals are received in order to form in a known manner a single or multi-dimensional image. In spectroscopy, information about the composition of the tissue is carried with the frequency component of the resonance signals.

An RF coil system provides the transmission of RF signals and the reception of resonance signals. In addition to the RF coil system which is permanently built into the imaging apparatus, special purpose coils can be flexibly arranged around or in a specific region to be examined. Special purpose coils are designed to optimize signal-to-noise ratio (SNR), particularly in situations where homogeneous excitation and high sensitivity detection is required. For example, for breast cancer screening a local breast coil is typically employed. A female patient is arranged in the prone position and the breast is positioned in the local breast coil beneath a specialized patient support on which the patient is laying.

MRI has relatively high sensitivity compared to x-ray mammography and ultrasound, but suffers from low sensitivity in determining whether a detected tumor is benign or malignant. The poor specificity coupled with low throughput of MRI breast screening limits MR based screening to high risk patients rather than general screening.

Due to the low specificity of these devices, they are adept for imaging the breast, however if the clinician locates a malignancy and determines a biopsy is necessary, the patient is relocated to patient support designed for biopsy. The procedure of repositioning the patient is cumbersome and time consuming for the patient, and it also introduces spatial position error into the biopsy procedure. When the patient is moved, he/she must be registered with the biopsy device to ensure the tissue from the malignancy is sampled rather than erroneously sampling the surrounding tissue.

The present application provides a new and improved method and system which overcomes the above-referenced problems and others.

In accordance with one aspect, an integrated MR imaging and interventional coil system is presented. The integrated system includes a support structure configured to be mounted in an MR imaging space and at least one lateral or medial coil device which define and adjust an anatomical receiving region between them. Each coil device includes at least one radiofrequency (RF) coil element and a housing having conformal surface to a patient anatomical portion received in the anatomical receiving region. The housing also includes apertures which define the trajectory for an interventional device into the anatomical portion.

In accordance with another aspect, a method immobilizing a patient during combined MR imaging and intervention is presented. The method includes positioning a patient with a selected anatomical region in an anatomical receiving region of a support structure. The method further includes immobilizing the patient anatomical portion between a lateral coil device and a medial coil device by independently translating the coil devices to adapt the anatomical receiving region to the received anatomical portion. This method can be used to immobilize a patient breast and/or axilla region and improve comfort for the patient when in the prone or supine position over the support structure.

One advantage resides in improved patient comfort.

Another advantage resides in improved patient safety.

Another advantage resides in that workflow for imaging and intervention is improved.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
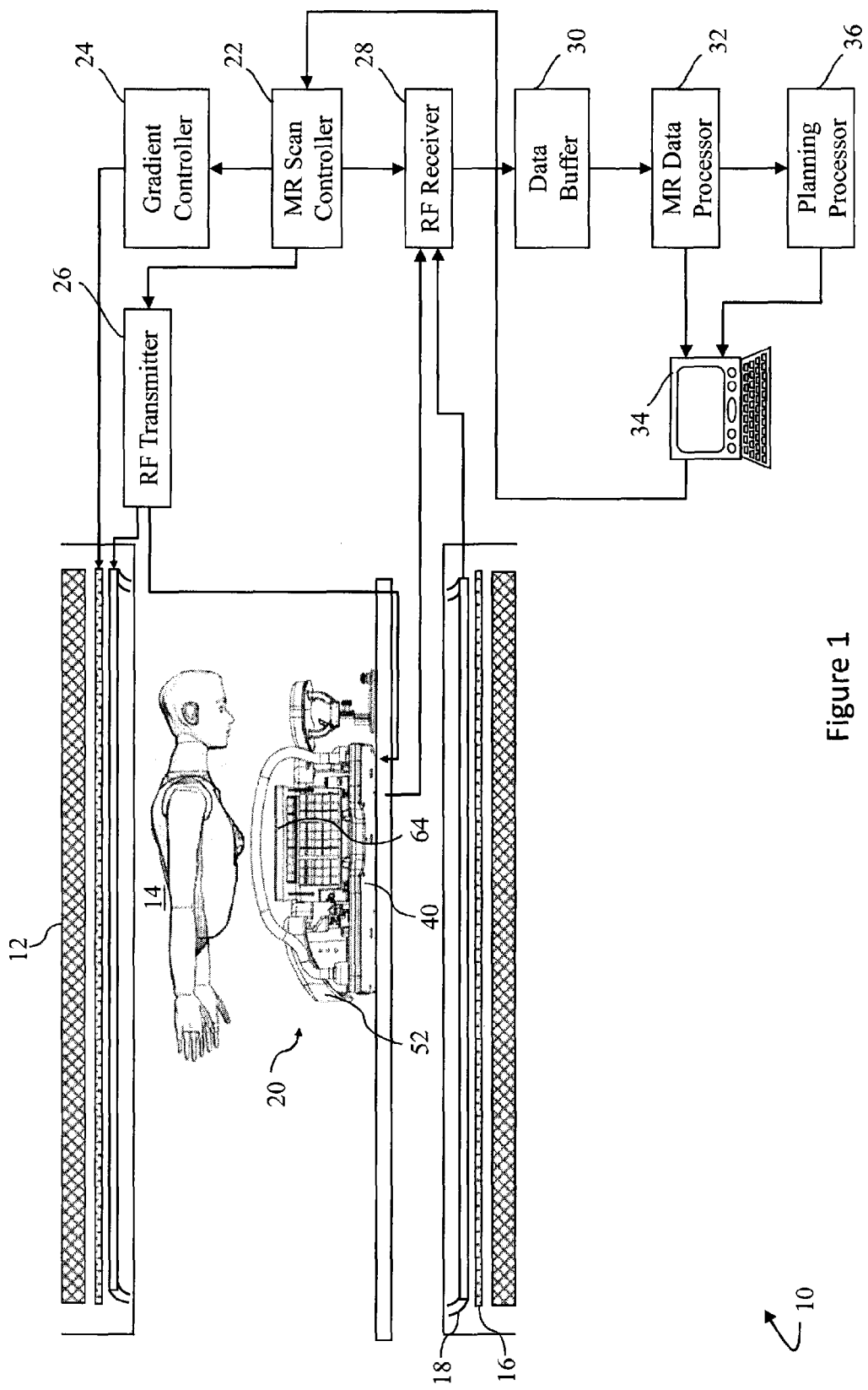
FIG. 1 is a diagrammatic illustration of an integrated MR imaging and interventional system with a localized diagnostic coil and interventional patient support.

With reference to FIG. 1, an integrated magnetic resonance (MR) imaging and interventional system 10 includes a main magnet 12 which generates a temporally uniform $B_0$ field through an examination region 14. The main magnet can be an annular or bore-type magnet, a C-shaped open magnet, other designs of open magnets, or the like. Gradient magnetic field coils 16 disposed adjacent the main magnet serve to generate magnetic field gradients along selected axes relative to the $B_0$ magnetic field for spatially encoding magnetic resonance signals, for producing magnetization-spoiling field gradients, or the like. The magnetic field gradient coil 16 may include coil segments configured to produce magnetic field gradients in three orthogonal directions, typically longitudinal or z, transverse or x, and vertical or y directions.

A radio-frequency (RF) coil assembly 18, such as a whole-body radio frequency coil, is disposed adjacent the examination region. The RF coil assembly generates radio frequency pulses for exciting magnetic resonance in aligned dipoles of the subject. The radio frequency coil assembly 18 can also serve to detect magnetic resonance signals emanating from the imaging region. The whole body coil can comprise of a single coil or a plurality of coil elements of an array as in a parallel transmit system. In parallel transmit systems, the k-space trajectory can be configured for a specific spatial sensitivity which ultimately shortens the overall pulse length. In one embodiment, the k-space trajectory determined by the gradient system, i.e. the gradient coil 16 and gradient controller 24, is the same for all transmit coils. In another embodiment, different $B_1$ pulses are determined individually for each transmit element of the transmit coil array. In addition to the whole-body RF coil 18, a localized diagnostic coil and interventional patient support 20 is disposed in the examination region to provide more sensitive, localized spatial encoding, excitation, and reception of magnetic resonance signals from an anatomical, receiving or imaging region 60 while providing dedicated interventional capabilities. The patient support 20 provides comfort to the patient during immobilization of an anatomical region. For example, during an MR imaging and biopsy procedure, the breast or chest is imaged while the patient is typically in prone position with the breast immobilized in a specialized patient support 20 with imaging capabilities which is placed on an examination table which translates in and out of the MR scanner examination region 14. If a tissue mass or malignancy is detected, the patient and the imaging patient support 20 are removed from the examination region 14 and a biopsy patient support 20 is then used to collect a tissue sample of detected tissue mass. During the biopsy procedure, the patient, the biopsy support, and biopsy needle are routinely imaged, often using x-ray fluoroscopy, which ensures an optimal trajectory of the biopsy needle to the tissue mass is achieved. This procedure may include several of iterations where the patient and biopsy needle are imaged together using the x-ray fluoroscopy system or in the MRI system using the whole-body RF coil 18 until the needle tip is positioned within the tissue mass to acquire a sample. The patient support 20 improves patient comfort and workflow by providing both imaging capabilities and interventional capabilities without having to reposition the patient between a dedicated imaging support and a dedicated interventional support. The patient support 20 also works for supine or side imaging procedures.

To acquire magnetic resonance data of a subject, the subject is placed inside the examination region 14, preferably at or near an isocenter of the main magnetic field. A scan controller 22 controls a gradient controller 24 which causes the gradient coils 16 to apply the selected magnetic field gradient pulses across the imaging region, as may be appropriate to a selected magnetic resonance imaging or spectroscopy sequence. The scan controller 22 also controls at least one RF transmitter 26 which causes the whole-body RF coil 18 and/or the patient support 20 to generate magnetic resonance excitation and manipulation of $B_1$ pulses. In a parallel system, the RF transmitter 24 includes a plurality of transmitters or a single transmitter with a plurality of transmit channels, each transmit channel operatively connected to a corresponding coil element of the array.

The scan controller 22 also controls an RF receiver 28 which is connected to the RF coil 18 and/or the patient support 20 to receive the generated magnetic resonance signals therefrom. The received data from the receiver 28 is temporarily stored in a data buffer 30 and processed by a magnetic resonance data processor 32. The magnetic resonance data processor can perform various functions as are known in the art, including image reconstruction (MRI), magnetic resonance spectroscopy (MRS), catheter or interventional instrument localization, and the like. Reconstructed magnetic resonance images, spectroscopy readouts, interventional instrument location information, and other processed MR data are stored in memory, such as a medical facility's patient archive. A graphic user interface or display device 34 includes a user input device which a clinician can use for controlling the scan controller 22 to select scanning sequences and protocols, display MR data, and the like.

The MR system 10 includes a planning processor 36 which determines the position of a tissue mass of interest relative to the patient support 20 and the examination region 14. With the position of the tissue mass and the patient support 20 known, the planning processor 36 determines an optimal trajectory for an interventional device, such as a biopsy needle, to reach the detected tissue mass.

Figure 2:
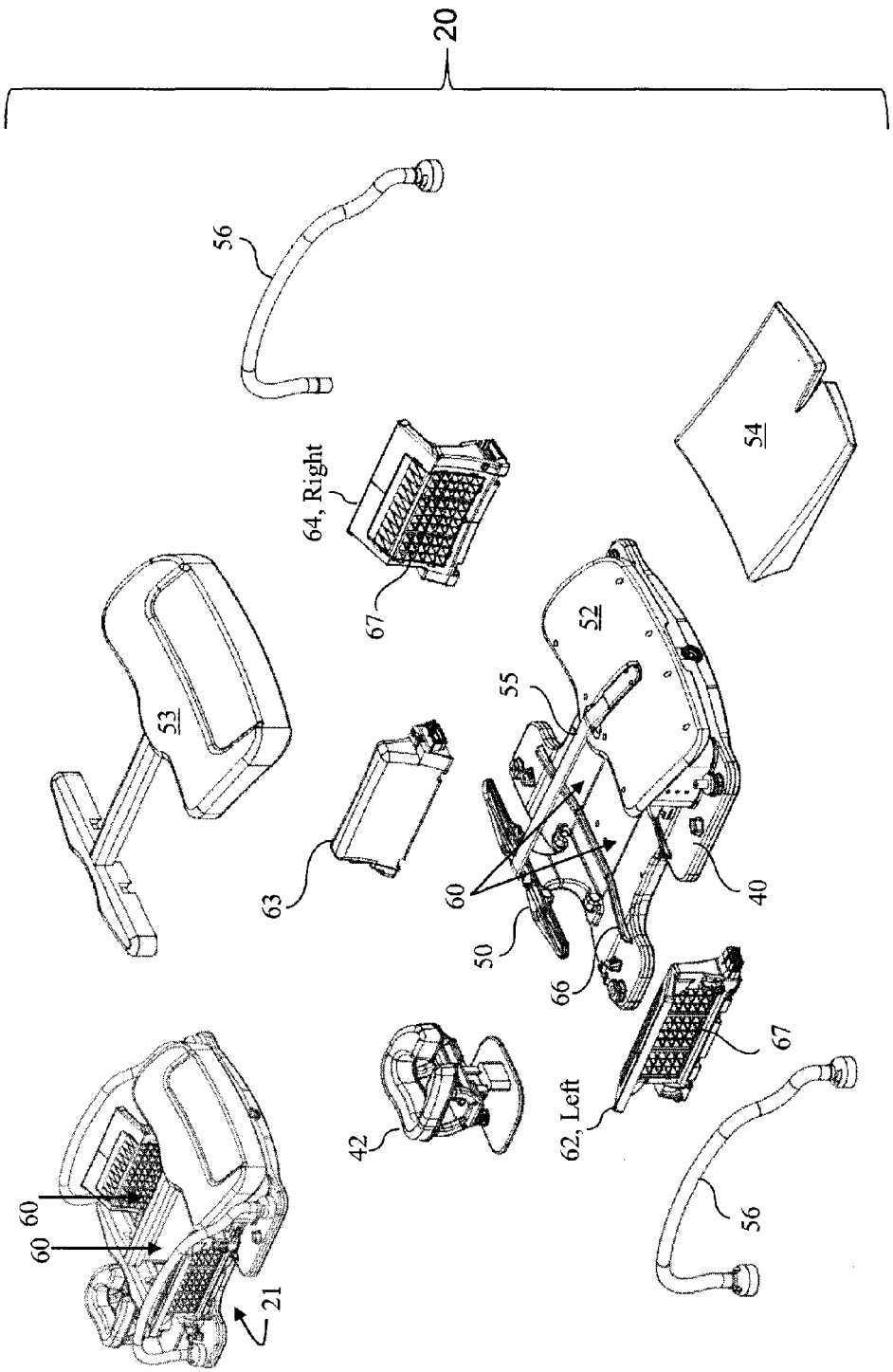
FIG. 2 is an assembled and exploded diagrammatic illustration of the localized diagnostic coil and interventional patient support.

With reference to FIG. 2, the patient support 20 is illustrated in an exploded view. An assembled patient support 21 is illustrated with all parts in place. When disassembled, the patient support 20 includes a coil base 40 which provides mounting structures and tracks for adjusting the position of various elements of the patient support 20. The support 20 includes various adjustable support structures to improve the patient's comfort during and imaging and/or interventional procedure. For example, the support 20 includes an adjustable headrest 42 which accommodates various neck lengths and head sizes. The headrest can be adjusted with a knob, or the like. The support 20 also includes adjustable clavicle supports 50 which support the patient's clavicle and upper chest at various x-positions, or heights. To accommodate various torso sizes, the support includes an adjustable torso support 52. As illustrated in FIG. 2, a one piece patient comfort pad 53 is attached to the clavicle supports 50 and the torso support 52 which conforms to the body and provides cushioned support to the shoulders, torso, and hips. In one embodiment, the torso support 52 includes an air bladder which inflates and deflates to accommodate the various torso sizes. However, other embodiments are also contemplated such as various sized torso supports which are interchangeably mounted on the patient support 20. To support the lower torso, waist, and upper legs, an adjustable accessory pad 54 ramps down from the torso support. Similar to the torso support 52, the accessory pad may include an air bladder to adjust the size to accommodate various patient sizes and geometry. However, employing multiple accessory pads of various sizes and shapes is also contemplated. The support structures, headrest 42, clavicle supports 50, the torso support 52, and accessory pad 54, are constructed from a multi-density foam to conform to the patient's anatomy and to reduce stress on pressure points.

The patient support also includes detachable hand rails 56 which assist the patient when getting into and out of the prone position on top of the patient support. The hand rails are detached during an imaging procedure to reduce image artifacts or during an interventional procedure to present a clinician unobstructed access to the patient's chest or breast.

Once the patient is comfortably situated in the support 20, the patient's anatomical region, under examination, is surrounded by a left lateral integrated MR diagnostic imaging and interventional coil device 62, a medial integrated MR diagnostic imaging coil device 63, and a right lateral integrated MR diagnostic imaging and interventional coil device 64. The coil devices 62, 63, 64 independently translate in the y-direction along tracks 66 in the coil base 40 to immobilize the anatomical region during imaging and interventional procedures. The lateral imaging and intervention coil devices 62, 64 move along an angled portion on the edges of the tracks 66, while the medial coil device 63 remains stationary on or moves along a central straight portion in the center of the tracks 66. The coil devices 62, 63, 64 are contoured to improve patient comfort. Though illustrated as a pair of lateral coil devices 62, 64, a single lateral coil can be used in conjunction with the medial coil device 63 to immobilize a single breast. An adaptable torso support sling 55 is attached to the clavicle supports 50 and the torso supports 52 to provide a flexible torso support that is adaptable to individual patients.

Figure 3:
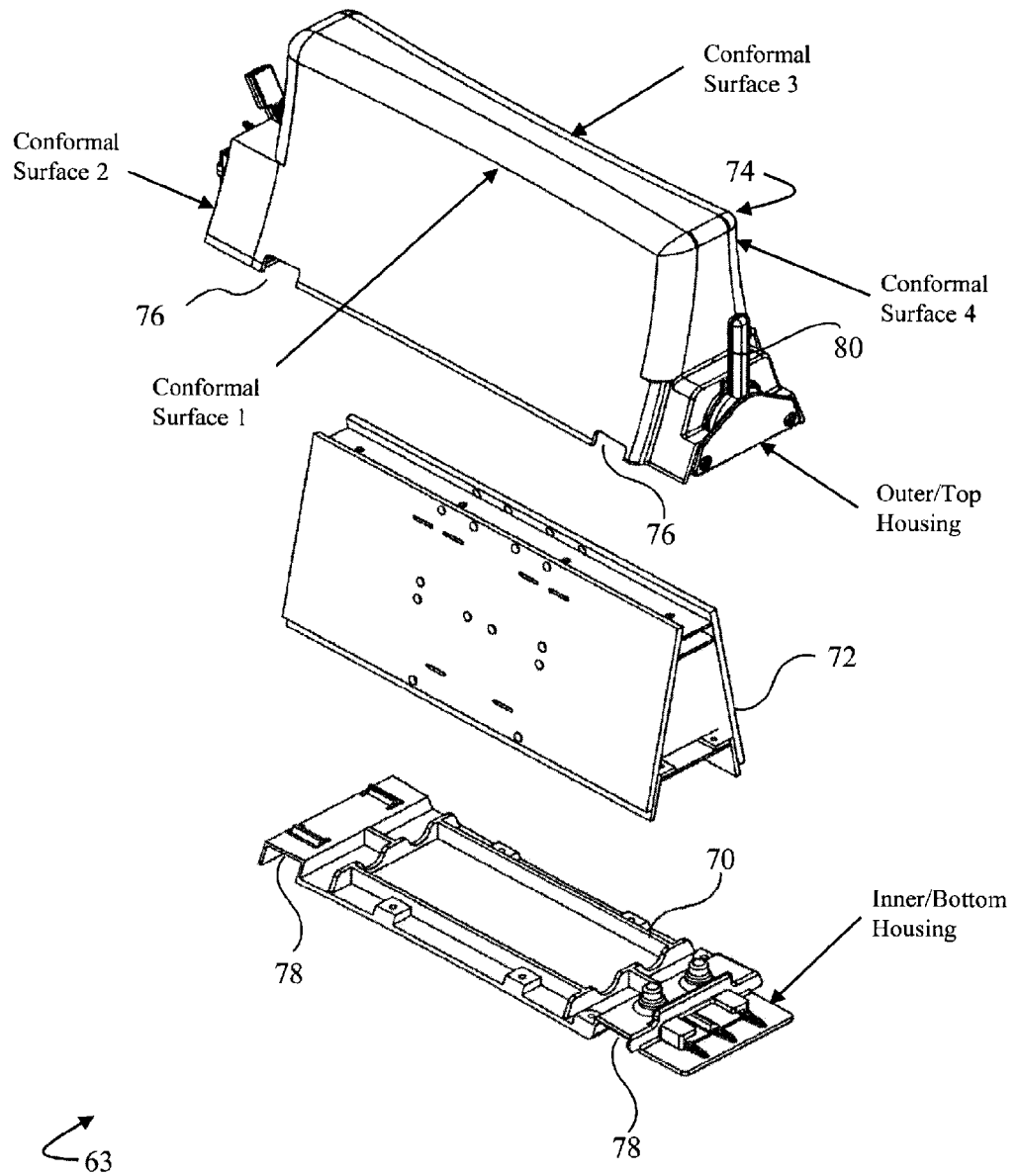
FIG. 3 is an exploded diagrammatic illustration of a medial integrated MR diagnostic imaging coil device as part of the localized diagnostic coil and interventional patient support.

With reference to FIG. 3, the medial integrated MR diagnostic imaging coil device 63 is illustrated in greater detail. In the illustrated embodiment, the medial coil device 63 includes an inner/bottom housing 70 which is attached to a center RF coil 72 surrounded by an outer/top housing 74. The center coil 72 provides localized spatial encoding, excitation, and reception of magnetic resonance signals and is permanently sealed within the housing pieces, which are non-ferromagnetic. The center coil 72 includes one or more coil loops to form various combinations of single loop coils, multi-loop coils, saddle-loop coils, and saddle-saddle coil. The outer/top housing 72 includes channels 76, and the inner bottom housing 70 includes channels 78 that slide along and interlock with the tracks 66 of the coil base 40 to translate and position the medial coil device 63 in the y-direction. Each channel is associated with a locking mechanism 80, such as a lever which exerts a frictional force on the corresponding track 66, to fix the y-position of the medial coil device 63. When examining the anatomical region, the medial coil device 63 is used in conjunction with the lateral integrated MR diagnostic imaging and interventional coil device 62, 64 to surround the region, e.g. breast, on both sides. The medial coil device 63 contains two opposite facing conformal surfaces to achieve a contoured fit with the human body during examination of the anatomical region.

Figure 4:
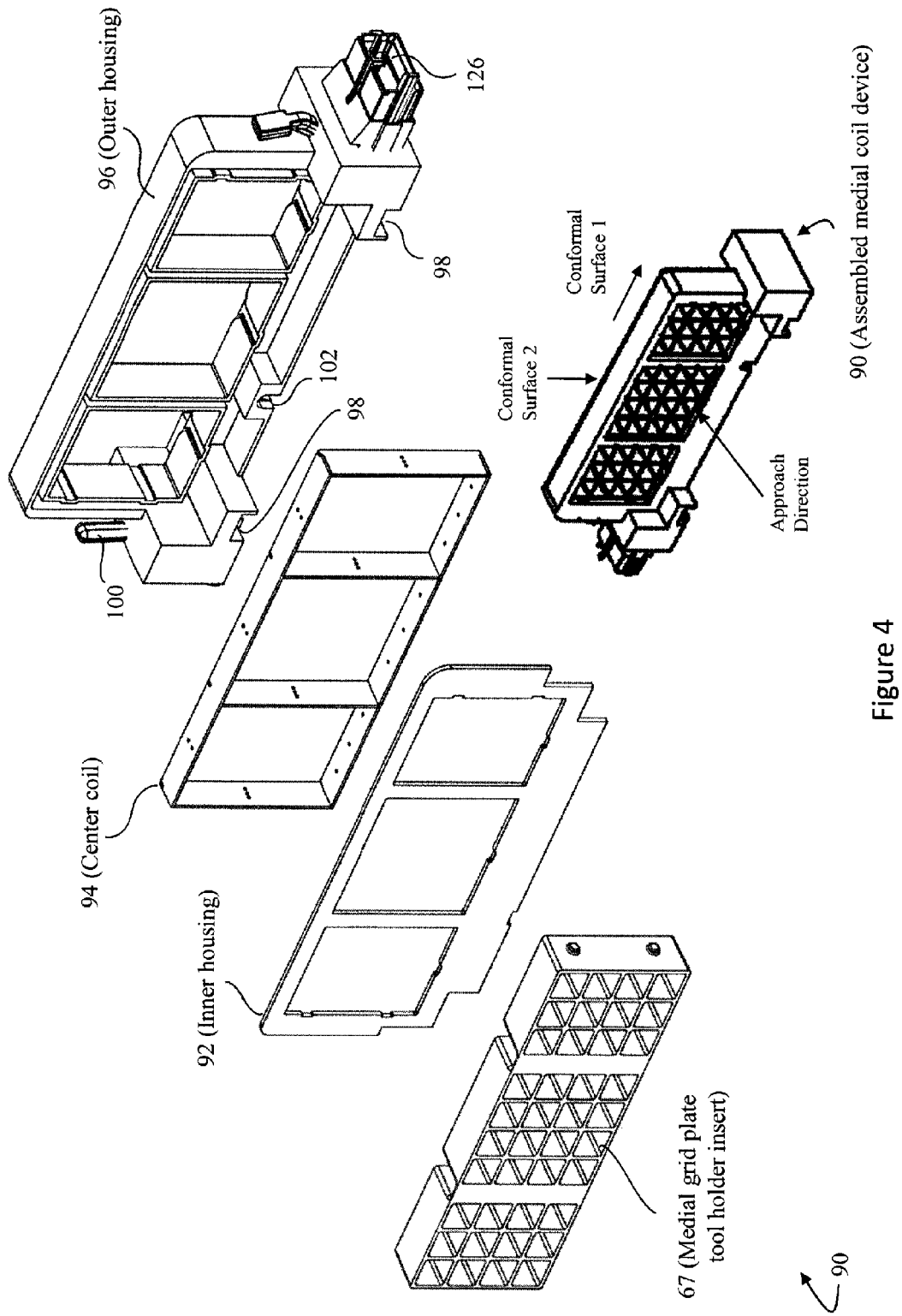
FIG. 4 is an assembled and exploded diagrammatic illustration of an alternative embodiment of a medial integrated MR diagnostic imaging coil device as part of the localized diagnostic coil and interventional patient support.

With reference to FIG. 4, another embodiment of a medial integrated MR diagnostic and interventional coil device 90 is illustrated. An assembled medial coil device 90 is illustrated with all parts in place. When disassembled, the medial coil device 90 includes a medial grid plate tool holder insert 67 which is attached to an inner housing 92, a center coil 94, and an outer housing 96. The center coil 94 provides localized spatial encoding, excitation, and reception of magnetic resonance signals and is permanently sealed within the inner and outer housing pieces 92, 96, which are non-ferromagnetic. The center coil 94 includes one or more coil loops to form various combinations of single loop coils, multi-loop coils, saddle-loop coils, and saddle-saddle coil. The outer housing includes the channels 98 which receive the tracks 66 of the coil base 40 to translate the medial coil device 90 in the y-direction. Each channel is associated with a locking mechanism 100, such as a lever which exerts a frictional force on the corresponding track 66, to fix the medial grid plate's y-position. When examining the breast region, the medial coil device 90 is used in conjunction with the lateral integrated MR diagnostic imaging and interventional coil devices 62, 64 to surround both breast regions on both sides. The medial coil device 90 can be used alternatively in place of medial coil device 63 to enable both imaging and interventional functions on the medial side of the anatomical region. The lateral coil device 64 contains two conformal surfaces to achieve a contoured fit with the human body, particularly the breasts, during examination of the anatomical region.

The tool holder insert 67 typically includes 40 grid locations, however more or less grid locations are also contemplated. The medial coil device 90 includes one or more fiducial markers 102 to register the grid plate's location relative to the examination region 14. The position information can be used to localize a detected tissue mass relative to the frame of reference of the patient support 20 and assist with a biopsy/interventional procedure. With the position of the tissue mass and tool holder insert 67 available, a clinician can position a targeting block 140 (FIG. 6) and an interventional instrument 142 (FIG. 6) for an optimal trajectory. The target block is inserted into one of the grids of the tool holder insert 67 to define an approach path and the instrument is inserted in the tool holder insert to perform a localized interventional procedure.

Figure 5:
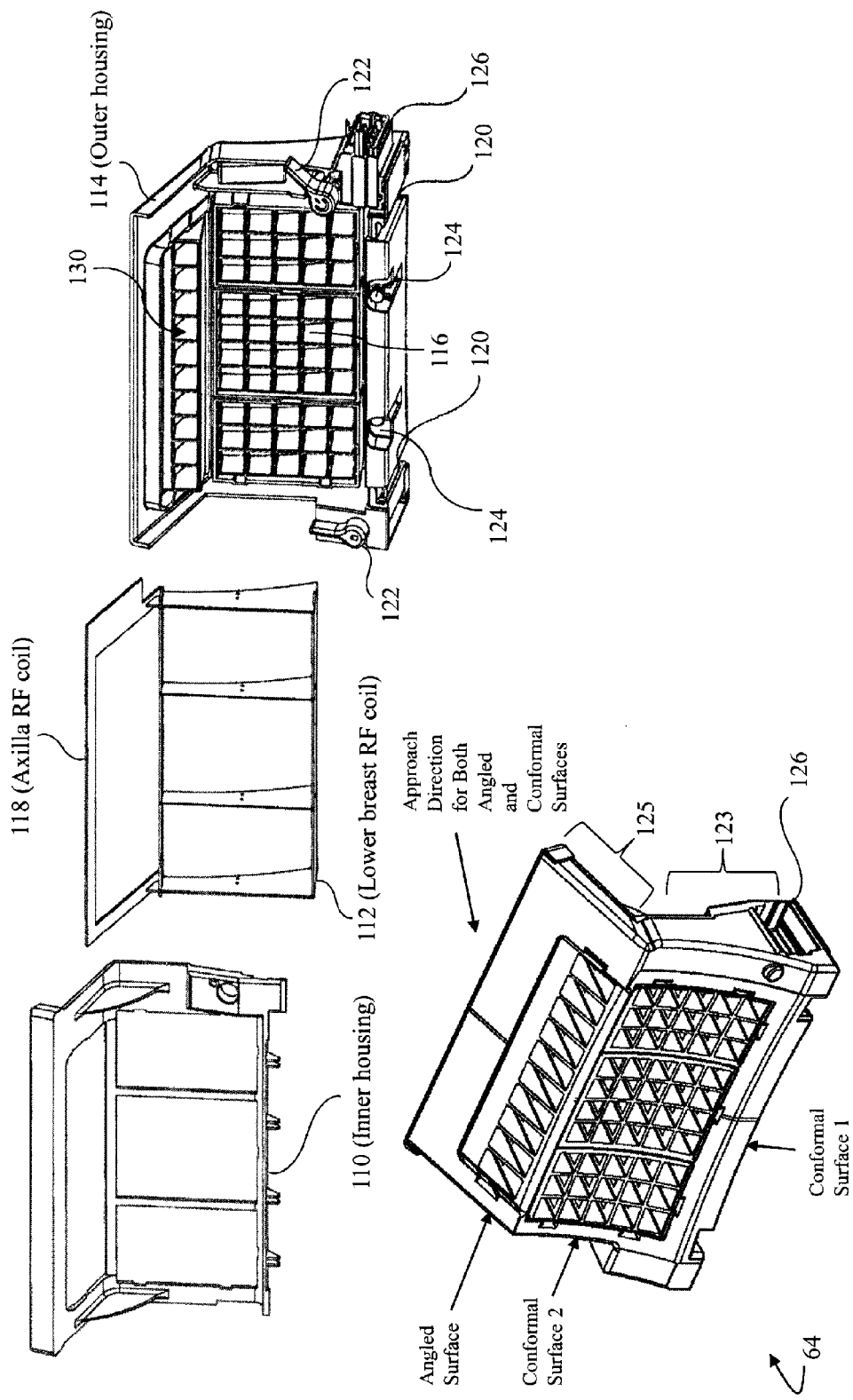
FIG. 5 is an exploded diagrammatic illustration of a lateral integrated MR diagnostic imaging and interventional coil device as part of the localized diagnostic coil and interventional patient support.

With reference to FIG. 5, the right lateral integrated MR diagnostic and interventional coil device 64 is illustrated. An assembled lateral coil device 65 is illustrated with all parts in place. When disassembled, the right lateral coil device 64 includes an inner housing 110, a lower breast RF coil 112, and an outer housing 114 which supports a lateral grid plate tool holder insert 116. The lower RF coil 112 provides localized spatial encoding, excitation, and reception of magnetic resonance signals and is permanently sealed within the housing pieces 110, 114, which are non-ferromagnetic. The lower RF coil 112 includes one or more coil loops to form various combinations of single loop coils, multi-loop coils, saddle-loop coils, and saddle-saddle coil. An upper or axilla RF coil 118 extends above the lower RF coil 112 and is angled relative to the lower RF coil 112. The tool holder grid insert 116 and lower and upper coils 112, 118 are permanently sealed within the housing pieces 110, 114. The lateral coil device 64 includes channels 120 that slide along and interlock with the tracks 66 of the coil base 40 to translate and position the lateral coil device 64 in the y-direction. Each channel is associated with a locking mechanism 122, such as a lever which exerts a frictional force on the corresponding track 66, to fix the medial coil device's y-position. The lateral coil device 64 contains a conformal breast surface in a breast portion 123 and an angled conformal axilla surface on an axilla portion 125 to achieve a contoured fit with the human body during examination of the breast region.

The tool holder grid insert 116, for example, includes 60 grid locations while more or less grid locations are also contemplated. The lateral coil device 64 includes one or more fiducial markers 124 to register the coil device's location relative to the examination region 14. The position information can be used to localize a detected tissue mass and assist with a biopsy/interventional procedure. With the position of the tissue mass and the position of the lateral coil device, a clinician can position a targeting block 140 and interventional instrument 142 for an optimal trajectory. As illustrated in greater detail in FIGS. 5, 6 and 7, the left lateral coil device 62 is a mirror image of the right lateral coil device 64. Alternatively, the left and right lateral units 62, 64 are the same and are rotated 180° to switch between left and right.

The lateral and medial coil devices 62, 63, 90, 64 communicate with the RF transmitter 24 and the RF receiver 28 via integrated connectors 126 which provide at least one of a digital, optical, inductive, and wireless communication to the RF receiver 28 or the RF transmitter 24 while the lateral and/or medial coil devices 62, 63, 90, 64 are being positioned. The integrated connectors 126 also form a data interface which carries at least MR signals including at least one of a sliding interconnection, a fiber optic connection, a wireless interconnection, and an inductive interconnection that does not interfere with the RF excitation signals or induced MR signals.

Figure 6:
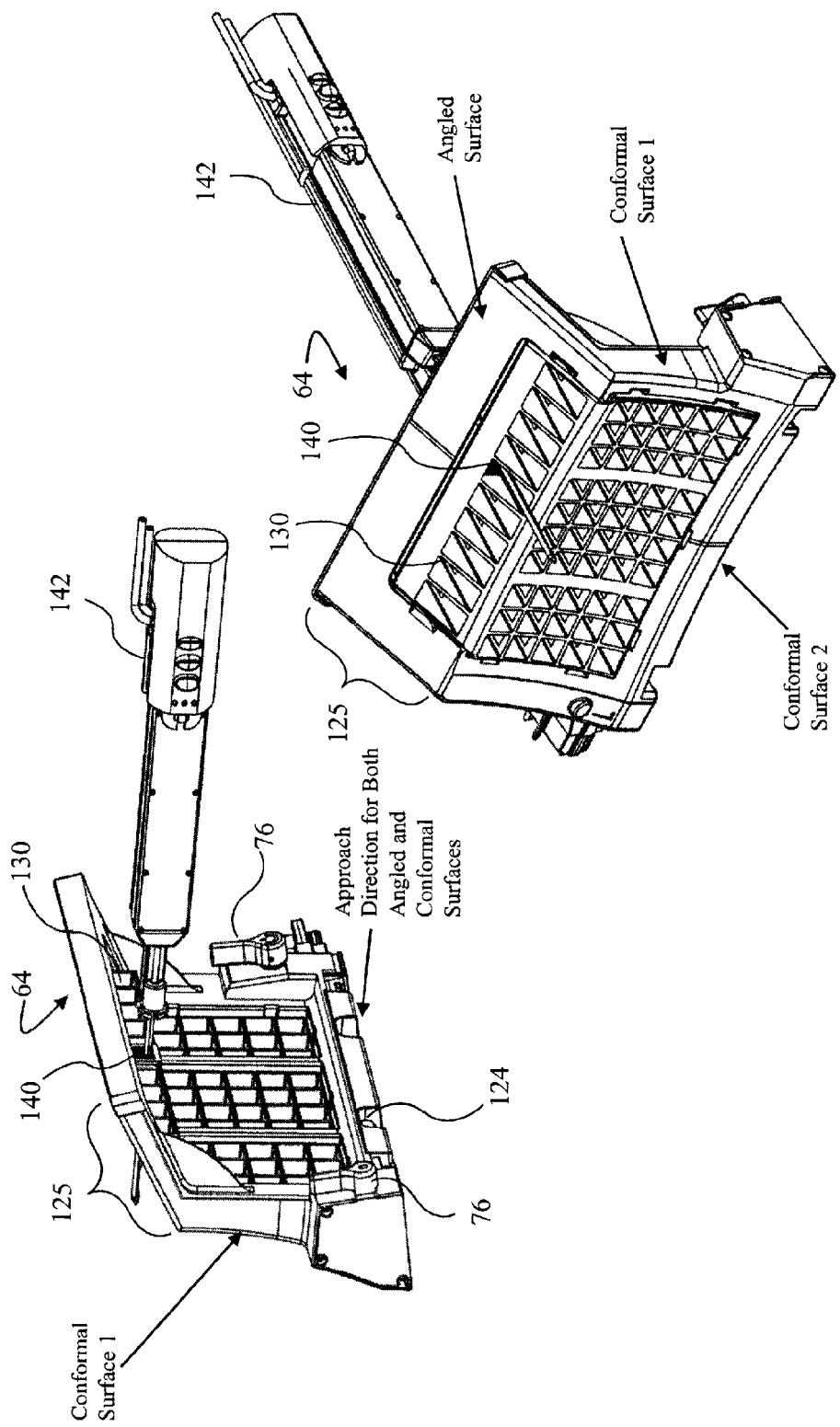
FIGS. 6 and 7 are assembled perspective views of the lateral integrated MR diagnostic imaging and interventional coil device with a targeting block and interventional device.
Figure 7:
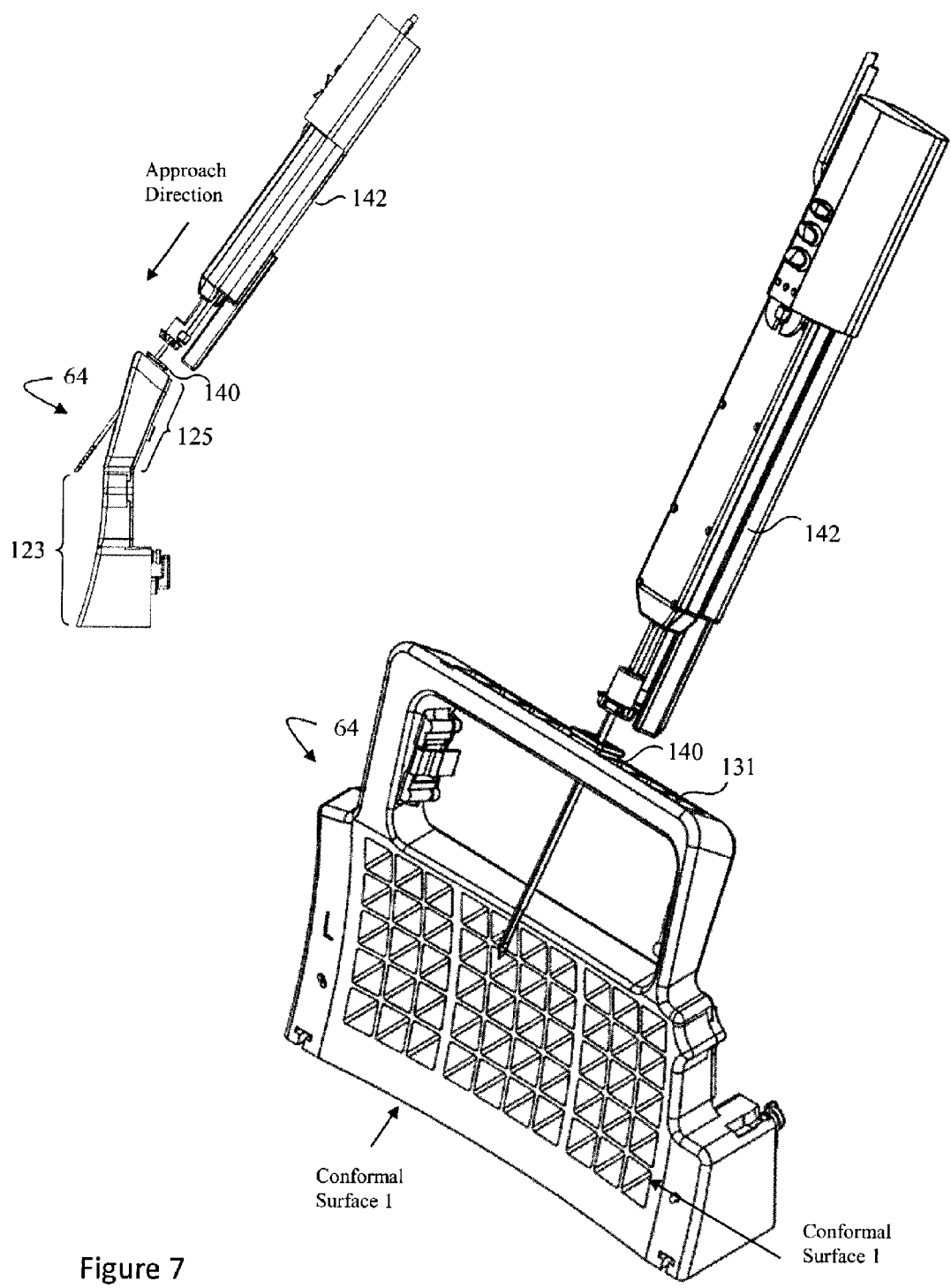

With reference to FIGS. 6 and 7, the right lateral integrated MR diagnostic imaging and interventional coil device 64 with a targeting block and interventional device is illustrated. The lateral coil device 64 includes an axilla grid plate 130 affixed to the axilla portion of the lateral coil device 64. The axilla grid plate 130 is configured to define paths generally perpendicular to the patient's axilla and provides grid locations which facilitate selection of an optimal trajectory to the patient's axilla. In the illustrated embodiment, the lateral coil device 64 includes, for example, 8 axilla grid locations.

The axilla grid plate 130 includes the integrated axilla RF coil 118 which provides localized spatial encoding, excitation, and reception of magnetic resonance signals. The axilla RF coil 118 is an extension of the lower lateral RF coil integrated into the lateral coil device 64 as illustrated in FIG. 5. Alternatively, the axilla RF coil 118 is a separate structure which is selectively connected to either the left or right lateral RF coil device 62, 64. Similar to the lateral and medial coil devices, the axilla grid plate 130 encapsulates the axilla RF coil 118 and corresponding electronics in a non-ferromagnetic housing which forms the conformal axilla grid plate 130. The axilla RF coil 118 includes one or more coil loops to form various combinations of single loop coils, multi-loop coils, saddle-loop coils, and saddle-saddle coil.

An interventional device 142, such as a biopsy needle or the like, is positioned generally perpendicular to a patient's axilla region. To make use of an interventional device 142 to perform an interventional procedure in a patient's axilla region, a targeting block 140 is inserted into one grid location of the axilla grid plate 130 which provides an optimal trajectory to a detected tissue mass of interest. The targeting block 140 inserted into any one of the grid locations includes one or more guide holes which more accurately define the selected trajectory of the interventional device 142 to a reach a target destination, such as a tissue mass or malignancy of interest.

Once the planning processor 36 determines the optimal trajectory based on the detected position of the tissue mass and the fiducial markers 102, 124 of the medial and/or lateral coil devices, the planning processor 36 determines the grid hole and type of targeting block 140 to be inserted in the guide hole. A plurality of the targeting blocks 140 are available with various angles, positions, sizes, and the like for orienting the selected interventional device 142 relative to the grid. Each type of targeting blocks 140 and each type of interventional instrument 142 are coded and stored in a database accessible by the planning processor 36. Once the grid position, type of targeting block, guide hole, and interventional instrument is determined by the planning processor for the selected intervention, the planning processor displays the corresponding information on the user interface 34 for the clinician. The information can be overlaid on the reconstructed image representations of the patient's anatomical region.

The axilla grid plate 130 is removably attached to the axilla coil housing so that different grid patterns can be selected. For example, the grid position of the axilla grid 130 illustrated in FIG. 6 is configured to guide the instrument along more horizontal trajectories. For more vertically oriented trajectories, the axilla grid 130 is removed and the target block 140 is mounted in a grid section 131.

Figure 8:
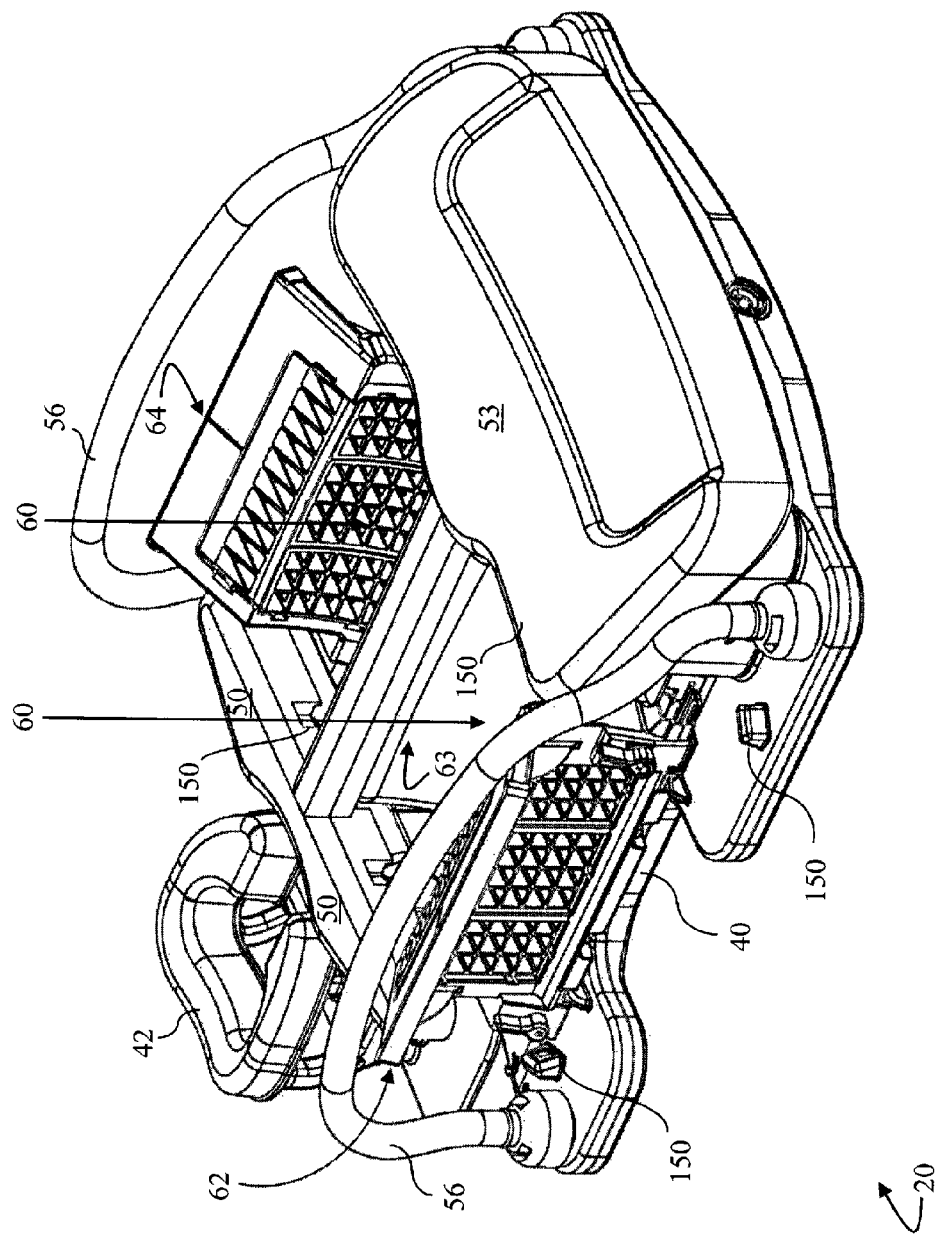
FIG. 8 is a diagrammatic illustration of another embodiment of the localized diagnostic coil and interventional patient support including a one piece patient comfort pad and a non-ferromagnetic lighting system.

With reference to FIG. 8, another embodiment of the patient support 20 including a non-ferromagnetic lighting system 150 is illustrated. In the illustrated embodiment, the coil base 40 includes the non-ferromagnetic lighting system 150, such as a fiber optic lighting system, to aid the clinician during an interventional procedure by maximizing illumination and minimizing shadowing. The lighting system 150 may also include LEDs, reflective elements, or similar lighting system. The lighting system 150 is powered by the MR system 10, a battery, an RF source coupled to the MR system 10, or an inductively coupled power source. The lighting system 150 is alternatively or additionally located on either the medial and/or lateral coil devices 62, 63, 90, 64, the clavicle support 50, or the torso support 52. The lighting system 150 illuminates the patient breast or chest in or near the anatomical receiving region 60. The intensity of the lighting system 150 is adjusted with a dimming switch, an adjustable lens, or the like which focuses the emitted light. The one piece patient comfort pad 53 is also shown in the illustrated embodiment, which attaches to the clavicle supports 50 and torso support 52 and provides cushioning support to the chest and torso.

Figure 9:
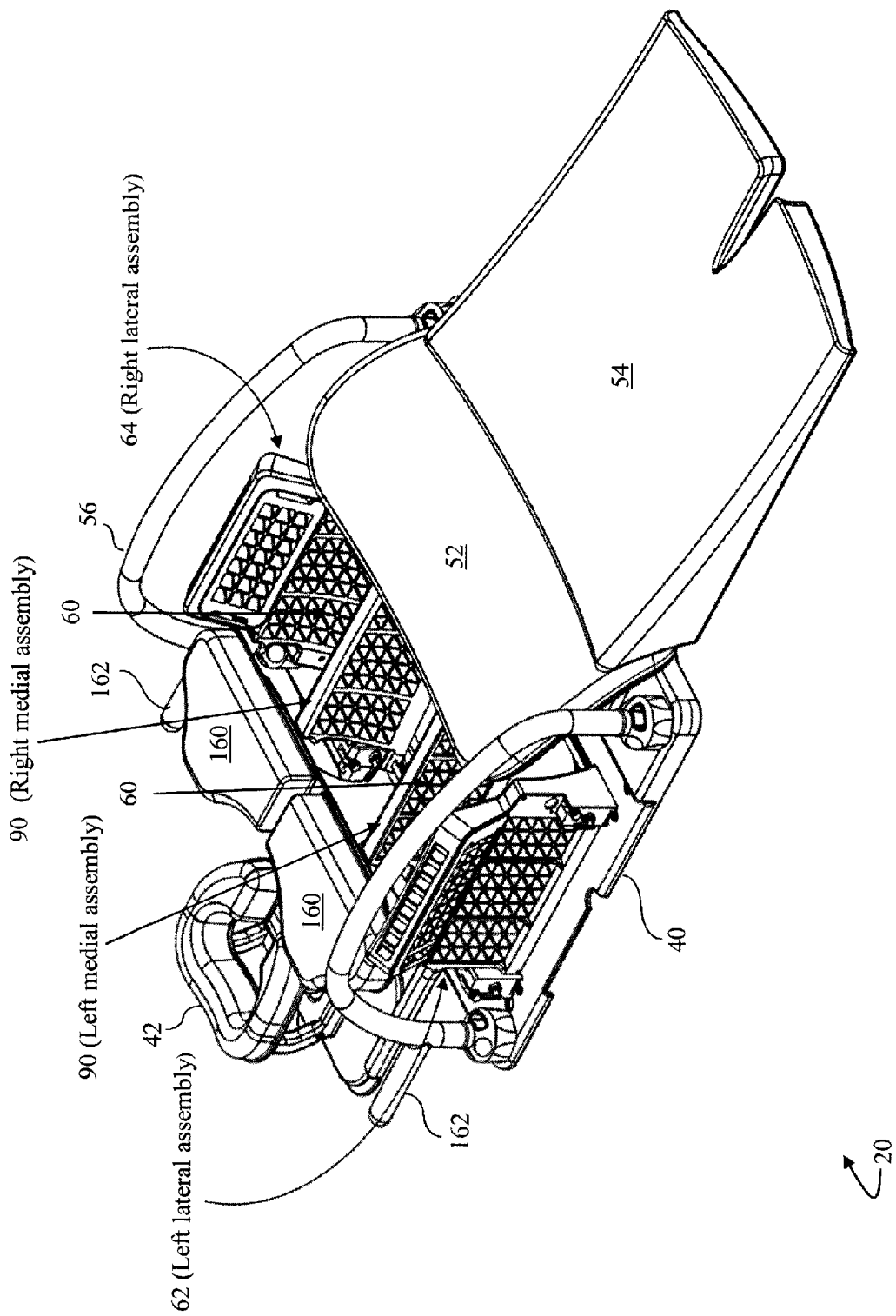
FIG. 9 is a diagrammatic illustration of another embodiment of the localized diagnostic coil and interventional patient support including adjustable clavicle support pads.

With reference to FIG. 9, another embodiment of the patient support 20 including clavicle support pads 160 is illustrated. In lieu of a one piece patient comfort pad 53, cushions 160 are placed on the adjustable clavicle supports 50. An adjustable accessory pad 54 ramps down from the torso support 53. The cushions 160 on the clavicle supports and accessory pad 54 may be of varying shapes and sizes and are constructed from a multi-density foam to conform to the patient's anatomy and to reduce stress on pressure points. The detachable hand rails 56 have been modified with an extra grip 162 to assist the patient when getting into and out of the prone position on top of the patient support.

In the embodiment of FIG. 9, two of the medial coil devices 90 are illustrated. The two medial coil devices 90 are independently movable along the tracks 66 for greater flexibility of adjustment.

Figure 10:
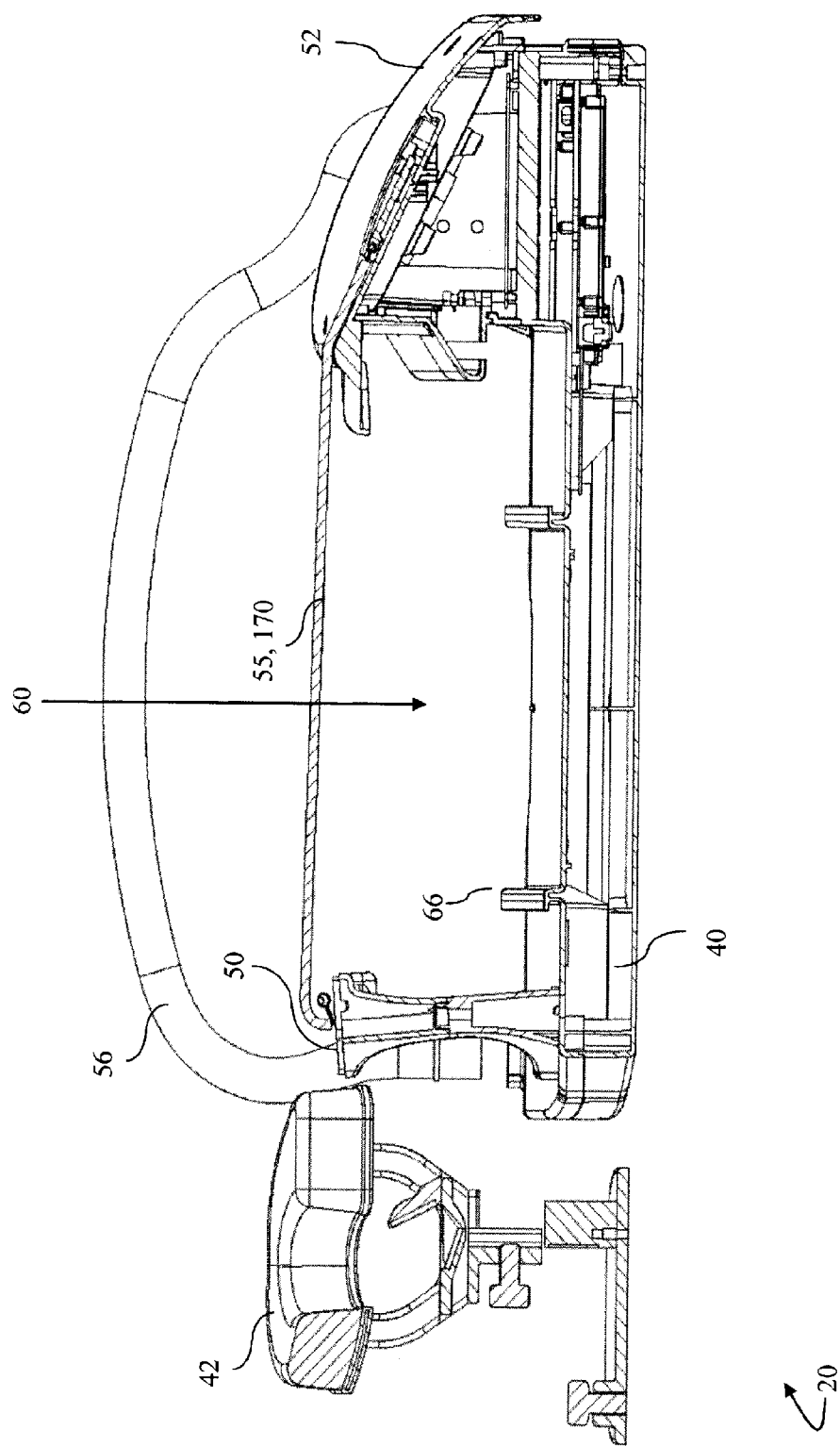
FIG. 10 is a side view diagrammatic illustration in partial section of another embodiment of the localized diagnostic coil and interventional patient support with a torso support sling and breast blocker.

With reference to FIG. 10, in another embodiment of the patient support 20, the adaptive torso support sling 55 and a breast blocker 170 is illustrated. The breast blocker 170 is a sling attached to the clavicle supports 50 and the torso supports 52 to provide a flexible support that is adaptable to individual patients. The breast blocker 170 also ensures the one breast does not interfere with the imaging or interventional procedure on the other. The breast blocker 170 compresses the other breast against the patient's chest. The breast blocker 170 is a mesh fabric that is movably positionable in a position to compress either breast or removed from the patient support 20 entirely. The breast blocker 170 permits unobstructed medial access to the other breast during an intervention.

Figure 11:
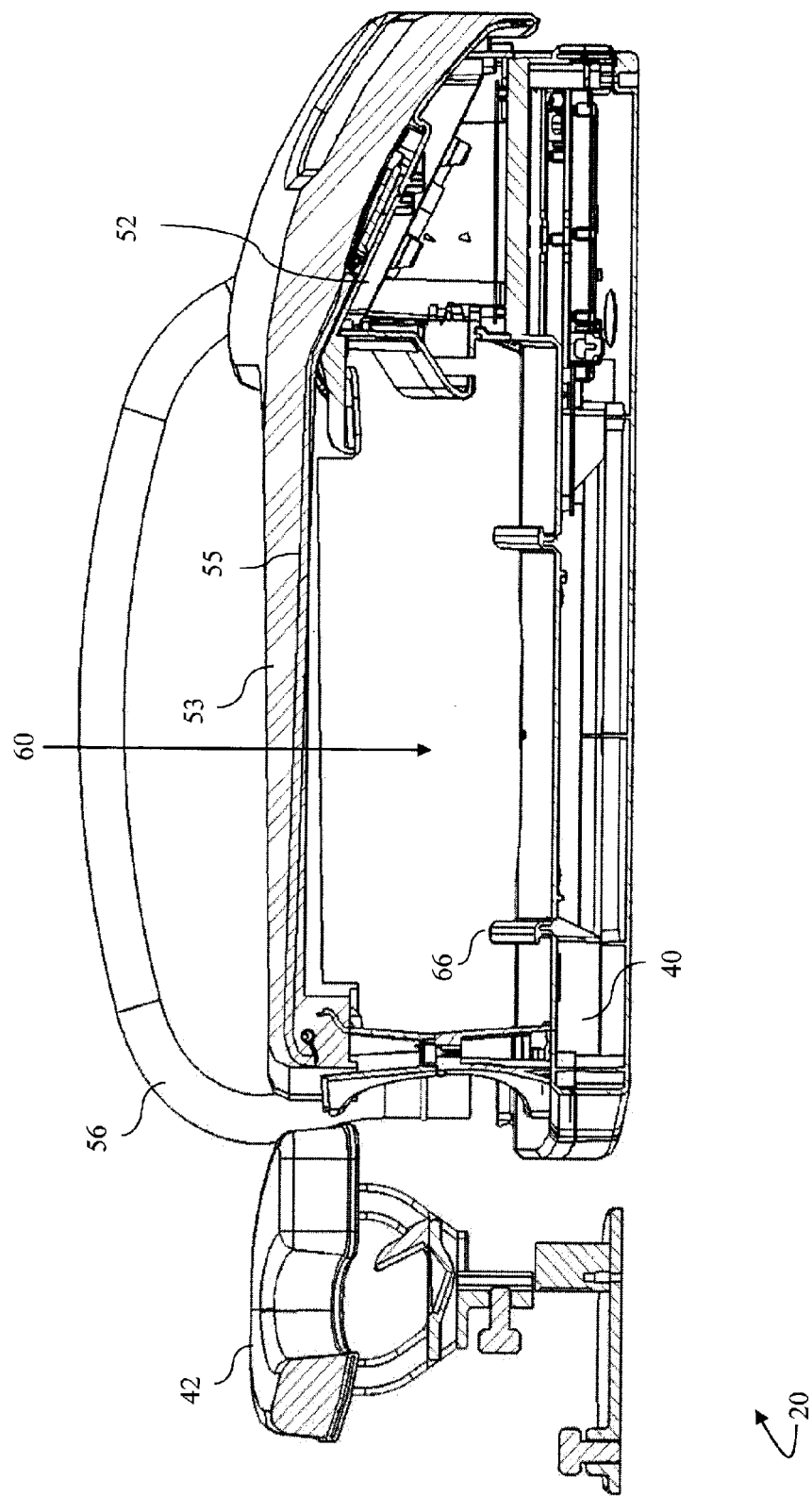
FIG. 11 is a side view diagrammatic illustration in partial section of another embodiment of the localized diagnostic coil and interventional patient support with the torso support sling, breast blocker, and a one piece patient support pad.

With reference to FIG. 11, another embodiment the patient support 20 with the one piece patient comfort pad 53 and the adaptive torso support sling 55 is illustrated. The combination of these support elements provides exceptional patient support and advantages when performing imaging and/or interventional procedures on the breast region.

Figure 12:
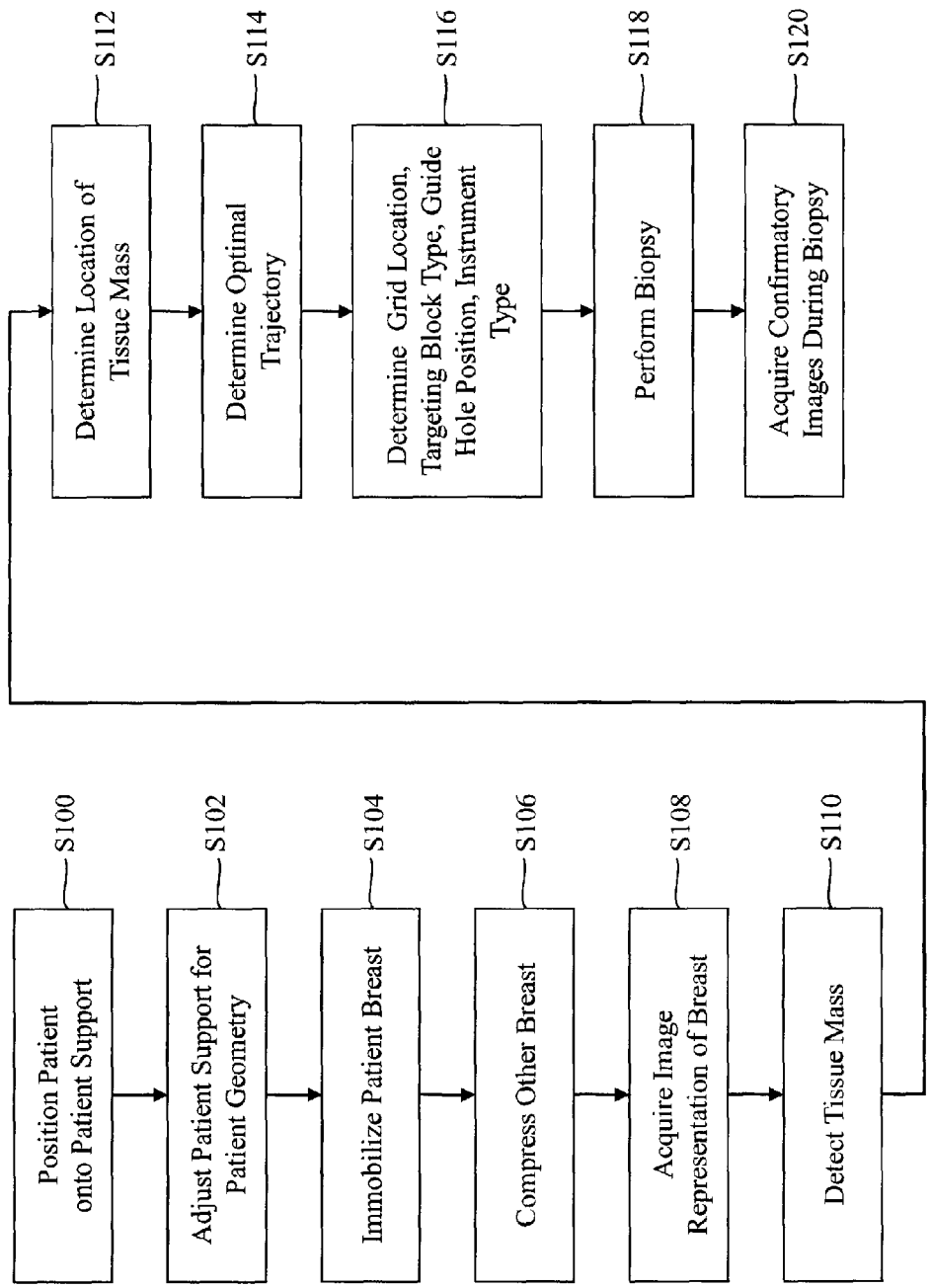
FIG. 12 is a flow chart of a method for magnetic resonance imaging and intervention with the localized diagnostic coil and interventional patient support.

With reference to FIG. 12, one advantage of the patient support 20 with integrated MR imaging coils and interventional support with lateral and medial coil devices which accommodate various targeting blocks and interventional devices resides in improvements in workflow. The patient can be imaged and operated on without having to be removed or repositioned in a patient support. With reference primarily to FIG. 12, and secondary reference to FIG. 1, an examination table is translated out of the examination region 14 and the patient support 20 is affixed the examination table. Once secured, a patient is positioned S100 prone on the patient support 20 with one or both of the patient's breasts disposed in anatomical receiving regions 60 between the lateral and medial coil devices 62, 63, 90, 64. The patient can assist his or herself into the prone position with the detachable hand rails 56. Once in the prone position, the headrest 42, clavicle support 50, torso support 52, and accessory pad 54, or one piece patent support pad 53 are adjusted to the patient's geometry S102 to improve comfort. Reducing patient discomfort my increase image quality and reduce intervention error because the patient is less likely to move around than when she is uncomfortable.

The patient breast is immobilized S104 between the lateral and medial coil devices 62, 63, 90, 64. The coil devices are independently translated. Once immobilized, the clinician locks the position of the lateral and medial coil devices by engaging the locking mechanism 80, 100, 122. In an optional step, the clinician can compress the patient's other breast S106, the breast not being examined, using the breast support 170. The breast support 170 is attached to the patient support 20 and extends across the unused portion of the anatomical receiving region 60. Compressing the patient breast against the chest may reduce inductive on the imaged breast which can affect image quality. It also allows for unobstructed access to the medial coil device 90 by the clinician during an interventional procedure.

With the patient situated and the breast immobilized, the clinician controls the MR scanner 10 to acquire an image representation S108 of the patient breast(s). The scanner controller 22 controls the RF transmitter 26 to transmit an RF excitation pulse to the whole body RF coil 18 and/or the RF coils 72, 94, 112, 118 integrated into coil devices 62, 63, 90, 64 and axilla grid plate 130 to induce an MR signal in the anatomical receiving region 60. The induced MR signal is then received by RF receiver 28 via the integrated RF coils. The RF receiver 28 conveys the received MR data to a temporary data buffer 30 from where the MR data processor 32 reconstructs the MR data into an image representation of the patient breast.

The planning processor 36 receives the image representation from the MR data processor 32 and automatically or semi-automatically analyzes the image representation to detect tissue masses or malignancy S110 in the patient breast. If a tissue mass of interest is detected, the planning processor 36 determines a location S112 of the detected tissue mass based on a known location of the fiducial markers 102, 124 of lateral and medial coil devices 62, 63, 90, 64. According to the location of the detected tissue mass, the planning processor 36 determines an optimal trajectory S114 for an interventional instrument 120, such as a biopsy needle. In one embodiment, the planning processor 36 determines S116 the grid location, targeting block 140 type, guide hole, and interventional instrument 142 to perform a selected intervention, such as a biopsy of the tissue mass. In another embodiment, the clinician selects an available interventional instrument 142 and the planning processor 36 determines the grid location, targeting block 140 type, and guide hole position accordingly.

The examination table is translated out of the examination region 14, and, without repositioning the patient in the patient support 20, the clinician disposes the determined targeting block 140 in the appropriate grid location according to the planning processor 36. In the case where the optimal trajectory is via the patient's axilla, the targeting block is disposed into one of the grid locations on the upper surface for the axilla grid plate 130. Once the targeting block 140 is positioned in the determined grid location and the interventional device 142 is positioned in the determined guide hole, the clinician performs the interventional procedure S118, such as a biopsy of the detected tissue mass. During the biopsy procedure, the clinician may opt to acquired confirmatory image representations S120 to ensure the interventional device 142 is following the determined optimal trajectory to the detected tissue mass. Generally the interventional procedure is performed with the patient, situated on the support 20, outside of the examination region 14. However, open c-arm type magnets permit the clinician to perform the intervention while the patient is still in the examination region 14. To acquire a confirmatory image representation, the examination table translates the patient on the support 20 back into the examination region 14 and an image representation is acquired. The patient is then translated back out of the examination region and the interventional procedure is resumed. The ability to acquire image representations and perform an interventional procedure seamlessly without repositioning the patient provides an improvement in workflow allowing procedures to be completed in a shorter time frame. Faster turn over for the interventional procedure incurs a cost savings because the clinician spends less time during the procedure and more imaging and interventional procedures can be completed.

The invention has been described with reference to the preferred embodiments. Modifications and alterations may

Having thus described the preferred embodiments, the invention is now claimed to be:

1. An integrated magnetic resonance (MR) imaging and interventional system comprising:
   a support structure configured to be disposed in an MR examination space;
   at least one coil device disposed on the support structure and defining an anatomical imaging region therebetween, the at least one coil device being mounted to translate relative to the support structure to adjust a size of the anatomical imaging region, the at least one coil device including:
      at least one radiofrequency (RF) coil element which induces MR and/or receives MR signals from the anatomical imaging region;
      a housing having conformal surface facing the anatomical imaging region, which conforms with a patient anatomical portion to be received in the anatomical imaging region, the housing encasing the at least one RF coil element; and
      wherein the at least one coil device defines at least one aperture in the conformal surface for accommodating a target block which defines a trajectory for an interventional device into the anatomical portion; and
      wherein the at least one coil device includes a lateral coil device and a medial coil device and an axilla coil and wherein the anatomical portion includes at least one of a patient breast and axilla region and the housing conformal surface is configured to conform at least one of the breast and the axilla region.

2. The integrated system according to claim 1, wherein the at least one coil device is translatable and removable from the support structure and configured to be mounted on the support structure and includes:
   one medial coil device and two lateral coil devices to define two anatomical imaging regions, each anatomical imaging region being between the medial coil device and one of the lateral coil devices, at least one of the lateral coil devices is integral with the axilla coil, the axilla coil being configured to induce MR and/or receive MR signals from the axilla region, the housing of the at least one lateral coil adjacent the at least one axilla coil being configured to conform to the axilla region an defining at least one aperture configured to accommodate a target block.

3. The integrated system according to claim 1, wherein the support structure further includes:
   a coil base supporting tracks on which the lateral and medical coil devices are slidably mounted to translate and immobilize the patient anatomy disposed in the anatomical imaging region.

4. The integrated system according to claim 1, wherein the RF coil element of the at least one coil device includes capacitive decoupled loop elements oriented parallel to an approach direction of an interventional device.

5. The integrated system according to claim 3, wherein the coil base further includes:
   a non-ferromagnetic lighting system configured to operate within a MR imaging magnetic field and to illuminate the anatomical imaging region.

6. The integrated system according to claim 1, wherein the housing of the lateral and medial coil devices further include:
   MR imageable fiducials which are imaged along with the patient anatomical structure in the anatomical imaging region during MR imaging; and
   an integrated connector which provides at least one of a digital, optical, inductive, and wireless communication between the coil devices and an RF transmitter and an RF receiver of an MR imaging system.

7. The integrated system according to claim 1, wherein the lateral and medial coil devices each further include:
   a data interface which carries at least MR signals, the data interface including at least one of a sliding interconnection, a fiber optic connection, a wireless interconnection, and an inductive interconnection.

8. The integrated system according to claim 1, wherein the patient support further includes:
   an adjustable head rest configured to adjustably support the patient's head and accommodates various neck lengths;
   an adjustable clavicle support configured to adjustably support the patient's clavicle and chest;
   an adjustable torso support configured to adjustably support the patient's torso and accommodate various torso sizes and contours;
   an adjustable sternum support configured to adjustably support the patient's sternum.

9. The integrated system according to claim 1, further including:
   a scanner controller which controls an RF transmitter to generate an excitation signal in the examination region and controls an RF receiver to receive induced magnetic resonance signals from the lateral and medial coil devices;
   a reconstruction processor which generates an image representation of the patient anatomical region received in the anatomical examination region from the received magnetic resonance signals; and
   a planning processor which localizes a detected tissue mass in the imaged patient anatomical region for biopsy in relation to at least one fiducial marker disposed in the lateral and medial coil devices.

10. The integrated system according to claim 1, wherein the lateral and medial coil device housings define a plurality of apertures configured to receive any one of a plurality of target blocks, the received target block defining a trajectory for an interventional device.

11. The integrated system according to claim 1, wherein the conformal surface is curved and contoured and conforms to the patient's breast to improve patient comfort.

12. The integrated system according to claim 2, wherein the axilla housing defines an opening configured to receive a removable axilla grid plate, the target block accommodated in the at least one aperture of the axilla coil being configured to define a trajectory through the opening, when the axilla grip block is removed, into the anatomical imaging region and when the axilla grid block is received in the axilla housing, the axilla grid plate is configured to accommodate the target block to define a trajectory generally perpendicular to the axilla.

13. The integrated system according to claim 2, wherein a lateral RF coil element is encased in a lateral coil device housing and the axilla coil is encased in an extension of the lateral coil device housing and extending above and angled relative to a portion of the lateral coil device housing that encases the lateral RF coil.

14. The integrated system according to claim 8, wherein the torso support includes an air bladder configured to inflate and deflate to accommodate various torso sizes.

15. An integrated magnetic resonance (MR) imaging and interventional system comprising:
   a support structure configured to be disposed in an MR examination space;
   a lateral coil device and a medial coil device disposed on the support structure and defining a breast imaging region therebetween, the lateral and medial coil devices being mounted to translate relative to the support structure to adjust a size of the breast imaging region, the lateral and medial coil devices each including:
      at least one radiofrequency (RF) coil element which induces MR and/or receives MR signals from the breast imaging region;
      a housing having a curved conformal surface facing the breast imaging region, which conformal surface conforms with a patient's breast to be received in the breast imaging region, the housing encasing the at least one RF coil element, wherein at least one of the lateral and medical coil devices defines at least one aperture in the conformal surface configured to accommodate a target block which defines a trajectory for an interventional device into the patient's breast; and
   an axilla RF coil element for receiving MR signals from an axilla region of the patient; and
   an axilla housing portion that encases the axilla RF coil elements, the axilla housing portion including a conformal surface configured to conform to the axilla region and defining a plurality of apertures configured to receive one of a plurality of target blocks, the target blocks defining a trajectory for an interventional device, the axilla housing portion extending from the lateral coil device housing away from the medial coil device.

16. The integrated system according to claim 15, wherein the axilla housing portion has an open central region and wherein the target block received in the apertures define a trajectory through the open central region, and further including:
   a removable axilla grid plate configured to be removably received in the open central region, the axilla grid plate defining a plurality of apertures configured to receive one of the plurality of target blocks.

17. The integrated system according to claim 15, wherein the support structure includes a base plate carrying tracks on which the lateral and medial coil devices are slidably mounted to adjust a spacing therebetween and further including:
   at least one of a LED and fiber optic lighting system mounted to the base plate and configured to be disposed in a magnetic resonance imaging region of a magnetic resonance scanner.

18. The integrated system according to claim 15, wherein the support structure includes:
   a torso support; and
   an air bladder configured to inflate and deflate to adjust the torso support to accommodate various torso sizes.

19. The integrated system according to claim 15, further including a mesh fabric which is configured to be attached to a clavicle support and a torso support to provide a flexible support to compress one of the patient's breasts to permit medial access to the other breast.

* * * * *